(12) United States Patent
Byrne et al.

(10) Patent No.: US 7,588,556 B2
(45) Date of Patent: Sep. 15, 2009

(54) SYRINGE

(75) Inventors: Phillip Owen Byrne, Newcastle Upon Tyne (GB); Penelope Rosemary Attridge, Middlesex (GB); Harry Raymond Ingham, Newcastle Upon Tyne (GB); John Polidoro, Manchester, CT (US); Spencer Kinsey, Manchester, CT (US); Chad Smutney, Manchester, CT (US)

(73) Assignee: ID-Tech Limited, New Castle Upon Tyne (GB)

( * ) Notice: Subject to any disclaimer, the term of this patent is extended or adjusted under 35 U.S.C. 154(b) by 499 days.

(21) Appl. No.: 11/155,888

(22) Filed: Jun. 20, 2005

(65) Prior Publication Data

US 2007/0005022 A1    Jan. 4, 2007

(51) Int. Cl.
*A61M 5/00* (2006.01)
*A61M 5/315* (2006.01)

(52) U.S. Cl. ........................................ 604/110; 604/218

(58) Field of Classification Search .................. 604/110, 604/218–238
See application file for complete search history.

(56) References Cited

U.S. PATENT DOCUMENTS

| | | | | |
|---|---|---|---|---|
| 5,000,737 A | * | 3/1991 | Free et al. .................... | 604/110 |
| 5,183,466 A | * | 2/1993 | Movern ....................... | 604/110 |
| 5,205,825 A | * | 4/1993 | Allison et al. ................ | 604/110 |
| 5,989,219 A | * | 11/1999 | Villas et al. .................. | 604/110 |
| 6,283,941 B1 | * | 9/2001 | Schoenfeld et al. .......... | 604/110 |
| 6,790,197 B2 | * | 9/2004 | Kosinski et al. .............. | 604/110 |
| 2003/0060759 A1 | * | 3/2003 | Lau et al. ..................... | 604/110 |

* cited by examiner

*Primary Examiner*—Nicholas D Lucchesi
*Assistant Examiner*—Victoria P Campbell
(74) *Attorney, Agent, or Firm*—Nixon & Vanderhye (57) ABSTRACT

Syringe having a plunger, a barrel and a restrictor mechanism between the shaft of the plunger and the barrel and including a first part engaged with the barrel for limiting movement of the first part with respect to the barrel in a first direction, and a second part. The restrictor mechanism and/or plunger shaft carries a formation for limiting movement of the restrictor mechanism with respect to the plunger in the first direction. The restrictor mechanism as a further member which restricts movement of the restrictor mechanism with respect to the barrel or plunger shaft in a second direction. A latch member prevents he further member from restricting movement of the restrictor mechanism with respect to the barrel or plunger shaft in the second direction until a predetermined point in an operation cycle of the syringe.

10 Claims, 9 Drawing Sheets

SYRINGE

TECHNICAL FIELD

The present invention relates to single use syringes, that is to say syringes which are intended to be used once and which are adapted in some way to prevent or at least to hinder further use.

BACKGROUND ART

Disposable syringes are known in which a cylindrical barrel formed of transparent plastics material receives a piston which is slidable within the barrel. A shaft, which may be of cruciform or other, e.g. circular, section extends from the piston to a plunger handle for enabling the piston to be displaced along the barrel in a first or proximal direction to cause injectable fluid or body fluid to be drawn into the barrel via an aperture at one end of the barrel, or in a second or distal direction to cause the fluid to be expelled out of the aperture or to be injected into a patient via a needle.

Syringes of this type are generally sold as disposable items and are intended to be used only once to negate the risk of transmission of diseases between patients. However, such syringes suffer from the drawback that it is difficult to prevent such syringes from being re-used, which re-use increases the risk of transmission of serious, life-threatening, conditions such as certain bacterial infections, viral hepatitis, and HIV.

Numerous designs have been proposed for syringes which are intended to negate or reduce the risk of the syringe being re-used. However, there are considerable challenges involed in designing a syringe which meets all desiderata, including, without limitation:

(a) allowing aspiration or flashback of blood to check for correct location of the needle in a patient;

(b) ability to deliver variable doses;

(c) smooth operation;

(d) simplicity of manufacture and use (e) ability to inject diluent (e.g. sterile water) into a vial of powdered/lyophilised drug, and/or allow agitation of vial or syringe contents to assist powdered drug to go into solution.

EP0925083B1 discloses a single use syringe comprising a barrel with an internal annular groove at the proximal end and a further annular groove near the distal end but spaced from it. The plunger is formed with an integrally moulded barb-like flange adjacent the head, which flange bears resiliently against the barrel interior wall. The flange is able to move unrestricted in either proximal or distal direction along the majority of the barrel interior wall; however, the flange is only able to pass the annular grooves in the distal direction. The syringe is supplied with the plunger not fully depressed, so that the restrictor flange is on the proximal side of the more distal of the two grooves. Liquid may be drawn up into the syringe until the flange encounters the proximal groove, which prevents the plunger being withdrawn completely from the barrel. Liquid may be discharged freely from the syringe by depressing the plunger, the flange passing just beyond the more distal of the grooves when the plunger head is moved to the extreme distal end of the barrel. In this position, the plunger is now prevented from being withdrawn again because the flange will not pass the groove in the barrel. This design is elegant and simple but suffers from a number of drawbacks, not least the fact that there will inevitably be a slight jolt as the flange passes the more distal of the grooves when an injection is being given, and this jolt is likely to be felt by a patient. Furthermore, because of the unrestricted movement of the plunger between the two grooves, the syringe could potentially be used again and again provided the plunger is never fully depressed. After unpacking a syringe, it is normal to cycle the plunger over a short distance to check that the plunger is free to move and, if it is not, to free it: sometimes there can be a degree of adhesion between the plunger head and the barrel due to the length of time of storage, or due to the effects of gamma sterilisation. This is particularly the case with plunger heads which have had silicone lubricant applied to them. During this movement it would be relatively easy to lock the plunger of this syringe by moving the flange past the distal groove. This design is the only one of which the inventors are currently aware which properly can be used to aspirate a flash of blood for checking needle position in a patient prior to injecting a drug.

U.S. Pat. No. 5,000,737 discloses a syringe having a single piece metal barbed restrictor element located between the plunger shaft and the cylindrical interior syringe barrel wall. The element has barbs facing towards the plunger which prevent movement of the plunger distally with respect to the element, and barbs facing the barrel which prevent movement of the element proximally with respect to the barrel. The restrictor element is initially located near the proximal end of the barrel; thus initial proximal movement of the plunger to draw up liquid is permitted as the plunger can slide past the restrictor in this direction. Subsequent depression of the plunger to deliver liquid is permitted because the restrictor can move distally with respect to the barrel, and hence when the plunger is depressed it carries the element with it. Further movement is of course prevented. This design has many similarities with some of the embodiments set out below; however, it does not permit aspiration of a flash of blood nor repeated movement to assist in reconstitution of lyophilised drug.

US2003/0060759 discloses a design which has similarities to that of U.S. Pat. No. 5,000,737, but also some important differences. It, too, utilises a single piece metal barbed restrictor element mounted between the plunger shaft and the barrel interior wall, and it employs outwardly facing barbs to restrict the motion of the element with respect to the barrel. In this design, however, the plunger shaft has a stepped form with a shoulder part way along it. The restrictor element has a spring tang which acts against the barrel and forces it against the plunger shaft. The restrictor starts out at the proximal end of the shaft; withdrawal of the plunger past the restrictor is permitted until an enlarged diameter portion of the shaft, near the plunger head, comes into engagement with the restrictor. At the same time, the proximal end of the restrictor snaps behind the shoulder on, the plunger; thereby movement of the plunger in either direction with respect to the restrictor is prohibited. The plunger can be depressed, carrying the restrictor with it to the distal end of the barrel, and then the plunger is incapable of further movement. This design is simple and has been used in a commercial vaccination syringe product. It suffers from the disadvantage that it may be used repeatedly, provided the user does not draw up the plunger to the point where the restrictor snaps into place on the reduced diameter part of the plunger shaft. Furthermore, once the restrictor has locked into place, which is of course the intention, aspiration of a flash of blood is not possible.

U.S. Pat. No. 5,222,942 discloses a design based on a ratchet system. A collar is installed in an initial distal position between plunger shaft and barrel. The plunger shaft is formed with annular ratchet teeth, and corresponding teeth are formed on the collar. The ratchet does not permit the plunger to be moved proximally past the collar, so when the plunger is initially drawn back in order to draw up liquid, it carries the collar with it to the extreme proximal end of the barrel where a formation on the barrel prevents the collar and plunger from being withdrawn completely from the barrel. The ratchet is such that the plunger may then be depressed past the collar to dispense liquid, and then of course the syringe is disabled. This design does not allow for aspiration of a flash of blood.

PCT/GB2004/005357 ('357), which is unpublished at the date of filing the present patent application, discloses a number of designs which are intended to allow for taking a flash of blood and possibly to allow for reconstitution of powdered drug. The designs described in '357 are intended to be simple and inexpensive and to have a smooth action which will not give rise to uncomfortable jolts when a patient is receiving an injection. The application is assigned to the assignee of the present application.

The designs desribed in '357 work on the principle of providing for a small amount of "lost motion" between a restrictor element and the syringe plunger, which allows for unlimited repeated distal and proximal movement over a distance which is just sufficient for the purpose of obtaining a flash of blood (or optionally for reconstitution of powdered drug). The distance may be carfully chosen so that it is sufficiently small to prevent, hinder or discourage repeated use of the syringe to deliver small doses of drug.

As stated above, achievement of all desiderata for a non reusable syringe in a single design is difficult, and there is normally a trade off between the complexity of the design and the the number of these goals which is achieved by the design. One potential issue with the designs described in '357 is that they will allow for drawing up and delivery of a volume of drug which is smaller than the usable volume of the syringe, and then drawing up and delivery of a further dose or doses until the total volume of the syringe has been used. For example, a 5 ml syringe may be used to draw up 3 ml of liquid drug and then administer it. At this point the restrictor element has been moved a corresponding distance along the plunger or barrel, but there remains a distance corresponding to 2 ml of syringe volume over which the restrictor may move before the syringe is fully disabled; therefore a further drawing up and delivery of a 2 ml dose of medicament is possible before the syringe is fully disabled Definitions Throughout this specification, the terms "distal" and "proximal" will be interpreted with respect to the user of the syringe, i.e. the person administering an injection. Thus the "proximal" end of the syringe is the open end into which the plunger is received, and the "distal" end is the nozzle/needle end.

The terms "usable length" and "usable extent" as used herein with respect to a syringe barrel mean that portion of the barrel's length over which the plunger head is intended to be able to travel in the course of normal use, that is to say in the course of drawing up and discharging/injecting fluid. In some cases this can be a relatively small proportion of the overall length of the syringe, e.g. if it is desired that a restrictor bobbin be inserted deep into the barel so as to make it harder for it to be removed by a user who may wish to deactivate the single use feature of the syringe.

The term "movement" as used herein, unless stated to the contrary, refers to movement substantially along the axis of the syringe, that is to say along the length of the syringe. Similarly the term "direction", as used herein with regard to the movement of components, refers to one or the other direction along the axis of the syringe, i.e. the proximal sense or the distal sense.

The terms "restricted" and "restrict" as used herein with respect to movement of a component of the syringe with respect to another component are intended to mean that a degree of restriction of movment is provided which is appropriate for the particular syringe. What is important is that the overall design of the syringe is such that a user attempting to circumvent its non-reuse features is prevented from doing so or is at least severely hampered. Different degrees of "restriction" may be required for different designs. In modified versions of some of the embodiments described herein, the plunger may have a weak point and be designed to break if a user tries to move the plunger in a restricted direction, thereby rendering the syringe inoperable. In a syringe incorporating such a feature, the force needed to move syringe components in a "restricted" direction may not be very great, e.g. 30-100N, provided the plunger is designed to break when a force lower than this is applied. A syringe in which the plunger did not have such a weak point may require that a greater force is able to be resisted.

SUMMARY OF THE INVENTION

According to the invention, a syringe comprises:
(a) a plunger including a plunger head and a shaft;
(b) a barrel;
(c) a restrictor bobbin located between the shaft and the barrel and having an outer barb, tine, serration or the like engaged with the barrel and oriented so as to limit movement of the bobbin with respect to the barrel in a first direction;
(d) the restrictor bobbin and/or shaft carrying a formation for limiting movement of the bobbin with respect to the plunger in the said first direction;
(e) the bobbin being provided with a further barb, tine, serration or other formation oriented or arranged so as to restrict movement of the bobbin with respect to one of the barrel and plunger shaft in a second direction opposed to the first direction;
(f) a latch member for disabling the said restricting function of the further barb, tine, serration or other formation until a predetermined point in an operation cycle of the syringe.

The said predetermined point in the operation cycle is preferably initial movement of the plunger in the distal direction. With such a syringe, a dose of medicament may be drawn up by moving the plunger proximally as normal. Then, in order to deliver the medicament, the plunger is moved distally; as soon as the plunger is moved a small distance distally (beyond the extent of any free unlimited repeatable movement as discussed below), the latch referred to above is disengaged rendering further substantial proximal movement of the plunger impossible. This renders the syringe unusable for any purpose except delivery of the dose of medicament which has already been drawn up, and this is true irrespective of whether the dose fills all or only a part of the usable volume of the syringe.

It will be appreciated that the prevention of movement of the plunger in the proximal direction means that drawing up of further liquid with the syringe is essentially prevented. However, it is contemplated that a degree of unlimited repeatable movement of the plunger in the proximal and distal directions over a small defined distance may be permitted, as described in detail in the '357 patent application discussed above. In fact, this is preferred, and the embodiments described below incorporate this feature.

In a preferred form, the barrel has a cylindrical interior surface substantially free of discontinuities between proximal and distal ends of a full range of usable movement of the plunger head in the barrel.

The said formation carried by the restrictor bobbin and/or shaft for limiting movement of the bobbin in the first direction preferably comprises a barb, tine, serration or the like carried by the restrictor bobbin and which is arranged to engage with the plunger shaft surface.

Preferably, the plunger and bobbin are freely slidable with respect to each other over a limited range of movement, or the plunger or bobbin have relatively movable parts, whereby repeated proximal and distal cycles of plunger head movement with respect to the barrel are permitted over a predetermined limited range which is less than the said full usable range of movement of the plunger head. If this feature is provided, it is preferred that the said repeated cycles of movement are permitted at least when the plunger is at or adjacent the said proximal end of the usable range of movement of the plunger head, and preferably over the full usable range of the syringe.

The said latch member, which is disengageable at a predetermined point in the operation cycle of the syringe, e.g. by an intial distal movement of the plunger, may take the form of a separate member secured to the barrel, preferably at or adjacent the proximal end of the usable range of the barrel, which in an engaged state extends between the plunger shaft and a portion of the restrictor bobbin. For example, the member may comprise a projection extending distally between the plunger shaft surface and a barb, tang, serration etc on the restrictor bobbin; initial distal movement of the plunger may cause the barb to slide off the latch member as the bobbin moves distally together with the plunger.

Alternatively, the said latch member may be provided as a separate member on or adjacent the proximal side of the plunger head, which in an engaged state extends between the barrel interior wall and a portion of the restrictor bobbin. Optionally the member may be an integral part of the plunger head. For example, the latch member may comprise a projection extending proximally from the plunger head, between the barrel and a barb on the restrictor bobbin. When the plunger is drawn back (proximally), the member remains between the barrel wall and the barb, but as soon as the plunger is moved distally, the barb slides off the latch member and engages with the barrel wall.

In a system where the restrictor bobbin is made in two relatively movable parts or a single part with a first region which may be deformed with respect to a second, the latch member may be provided on one of the two parts or regions. For example, it may comprise a projection extending from one of the parts or regions of the restrictor bobbin and, in an engaged state, between the plunger or barrel surface and a barb, tine, serration (or the like) on the other part or region of the bobbin.

The latch member is preferably made from a material which is harder than the material of the syringe barrel and plunger shaft, such that the said barb, tine, serration, etc may not penetrate the latch member material. Preferably, the latch member material is such that the barb, tine, serration etc will slide over it relatively freely, preferably even when the barb, tine serration, etc is biased against the latch member. The latch member is preferably metal, more preferably stainless steel. The barb, tine, serration, etc is preferably metal, e.g. stainless steel. The syringe plunger and/or barrel are preferably of plastics material, e.g. polypropylene.

A syringe barrel which is substantially free of discontinuities over its usable extent helps to make for smooth operation of the plunger, especially during the delivery stroke when an injection is being given to a patient. Any jolts in the operation of the syringe during the delivery stroke are normally felt by the patient, and it is desirable to avoid this happening. Discontinuities in the inner cylindrical surface which would not be engaged by the sealing face of the plunger head (piston) in normal use or in use during the delivery stroke are not considered to be in the "usable extent" of the barrel. For example, a reduced diameter portion of the barrel may be provided at the far proximal end of the usable extent of the barrel for preventing complete withdrawal of the plunger from the barrel: this would not be considered part of the "usable extent".

The provision of free relative movement of the restrictor bobbin and shaft over a limited predetermined extent allows repeated movement over a distance which is sufficiently small not to allow repeated injections with the syringe, or at least only to allow repeated injections of smaller quantities of fluid than the syringe would normally be capable of delivering. This degree of movement may be sufficient to allow for aspiration/flash-back of blood for checking needle location in a patient. Alternatively or in addition, this degree of movement may be sufficient for repeated movements to assist reconstitution of powdered/lyophilised drug into solution.

It is preferable, though not essential, that the feature which allows aspiration of blood be operative at any position of the plunger so that the feature can be used whatever volume of injectable is contained in the syringe and also may be used to check the needle position in a patient prior to drawing a blood sample, i.e. when the syringe is substantially empty and the plunger in a distal position with respect to the barrel. Therefore, preferably the said limited repeated cycles of distal and proximal movement referred to above are permitted at substantially every relative position of the plunger and barrel over a the usable range.

The distance over which repeated movement is possible is, desirably, sufficient to aspirate a small volume of blood from a patient so as to check the position of the needle. All that is required for this function normally is that the aspirated blood be visible in the syringe. Factors which may need to be taken into account in determining the degree of movement required for this function may include, without limitation:

(a) the internal volume of the needle;

(b) if the needle is a separate entity, the internal volume of the syringe nozzle onto which the needle hub fits and any volume between the end of the nozzle and the internal base of the needle hub;

(c) any volume between the internal end of the syringe barrel and the plunger face when fully depressed;

(d) any "end float" of the plunger head: if the the plunger head is a separate entity from the shaft, then a certain amount of free play between the two is sometimes required to ensure the head "snaps on" to the shaft in manufacture;

(e) resilient deformation of the plunger head;

(f) the pressure drop which it is necessary to create to be sure that blood is aspirated;

(g) the volume of blood which needs to be present in the syringe barrel for the user to be able to discern its presence;

(h) a safety/error factor;

(i) the distance over which the user can discern movement easily: the "ergonomics" of the feature; and (j) the diameter of the syringe barrel and plunger head.

The last of these points particularly will have a large effect on the volume as swept by the plunger head which corresponds to the distance over which the said repeated movement is possible.

The smallest possible volume for achieving this effect is about 10 microlitres: this might be the case e.g. if a short and thin (e.g. 1 cm, 30 gauge) needle is used which is moulded into the syringe barrel and if a plunger with an integrally moulded head is used, etc. In a 10 ml syringe this would correspond to 0.1% of the 10 ml swept volume of the syringe which equates to 0.1% of the usable length of the syringe. This is not precise since the usable volume of a syringe is often slightly more than its stated or graduated volume.

Normally a volume considerably greater than 10 microlitres would be required. For example, a large needle (e.g. 5 cm long, 18 gauge) may have an internal volume of approximately 50 microlitres. A standard luer nozzle has a dead space of about 50 microlitres and there will be additional dead space between the end of the nozzle and internal end of the needle hub. The plunger head of some syringes may have an end float of up to 1 mm which could correspond in a 10 or 20 ml syringe to 500 microlitres or more. In a 10 or 20 ml syringe a very small volume of blood may be more difficult to see in which case as much as 500 microlitres may be required. Adding these factors together with an allowance for error and for creating the pressure drop for withdrawing the blood might give a volume of as much as 2000 microlitres. In a 20 ml syringe this would correspond to 10% of the usable (graduated) swept volume of the syringe.

If it is desired that the syringe plunger should be capable of repeated movement of sufficient extent to agitate a drug powder and diluent mix, then it may be desirable to increase this range to as much as 50%. Of course, the larger the range of free movement, the greater the danger that this movement makes the syringe too easily re-usable for injecting drugs or other uses. The figure of 50% would probably be much too high for a 10 or 20 ml syringe, but for a very small syringe (0.5 ml or less) it may not be totally unreasonable from the point of view of preventing or at least hindering further use.

It can be seen that a large range of possibilities exist depending on the exact use to which the syringe is to be put. However, for most situations, a volume of between 50 and 500 microlitres would be preferable. 50 microlitres might be appropriate e.g. for a 5 ml syringe with a very small integral needle and where agitation of reconstituted drugs is not required. It would probably be desirable for this quantity to be more in the region of 100 or 150 or 200 microlitres, however, to allow a good margin for safety, human error, manufacturing tolerance, etc. 1000 microlitres might be appropriate for the same syringe where the ability to agitate reconstituted drugs is desirable, though this may still provide too great an opportunity for re-use of the syringe, and 500 microlitres may be more preferable.

Preferably, the distance over which the said repeated movement is possible is between 0.1% and 50% of the said barrel usable length, preferably between 1% and 20%. The lower end of this range might preferably be increased to 2%, 3% or 4% based on the example discussed above. The upper end of this range might preferably be reduced to 10% based on the example discussed above. However, these ranges should not be taken as limited to the particular syringe sizes discussed above which are presented by way of example only.

Accordingly, the said distance over which repeated movment is possible corresponds to a swept volume which is between 10 and 2,000 microlitres, preferably between 50 and 1000 microlitres, more preferably between 100 and 500 microlitres, or other absolute volume ranges corresponding to the percentage values of the total syringe volume mentioned above, for syringe total usable/measurable volumes of 0.5 ml, 1 ml, 1.5 ml, 2 ml, 2.5 ml, 3 ml, 5 ml, 10 ml and 20 ml.

The penultimate item in the above list of factors which may affect the desirable range of repeatable movement, factor (i), may require that a minimum distance is determined by what a user can practically work with. A reasonable range might be 0.5 mm to 20 mm, preferably 1 mm to 15 mm, more preferably 1.5 mm to 10 mm, still more preferably 2 mm to 7 mm or about 3 mm or 4 mm.

A number of embodiments of the invention will now be described, by way of example only and not in any limitative sense, with reference to the accompanying drawings, in which:

FIG. 1b is an elevation of the component of FIG. 1a;

FIG. 1c is a perspective view in a second direction of the component of FIG. 1a;

FIG. 1d is a perspective view in a third direction of the component of FIG. 1a;

FIG. 2b is an elevation of the component of FIG. 2a;

FIG. 2c is a perspective view from a different direction of the component of FIG. 2a;

FIG. 5a is perspective view of a plunger lock component of a second embodiment of the invention;

FIG. 5b is a perspective view in a different direction of the component of FIG. 5a;

FIG. 6a is a perspective view of a barrel lock component of the first embodiment;

FIG. 6b is a perspective view from a different direction of the component of FIG. 6a;

All the following embodiments are described principally with respect to a syringe having a nozzle, e.g. a luer connector, for attachment of a cannula, hypodermic or other needle or catheter line, etc. It will be appreciated that in every embodiment this nozzle could be replaced by a needle which is incorporated into the syringe at manufacture, e.g. moulded into the plastic of the barrel. It should also be understood that all of the following embodiments may be adapted to provide a frangible or weakened region on the plunger which is designed to break if excessive force is applied to the plunger. Alternatively the plunger may be made in more than one part which parts are designed to separate when excessive force is applied. In either case, the syringe is rendered inoperable or at least substantially inoperable.

A first emodiment will now be described with reference to FIGS. 1 to 4.

Figure 1A:
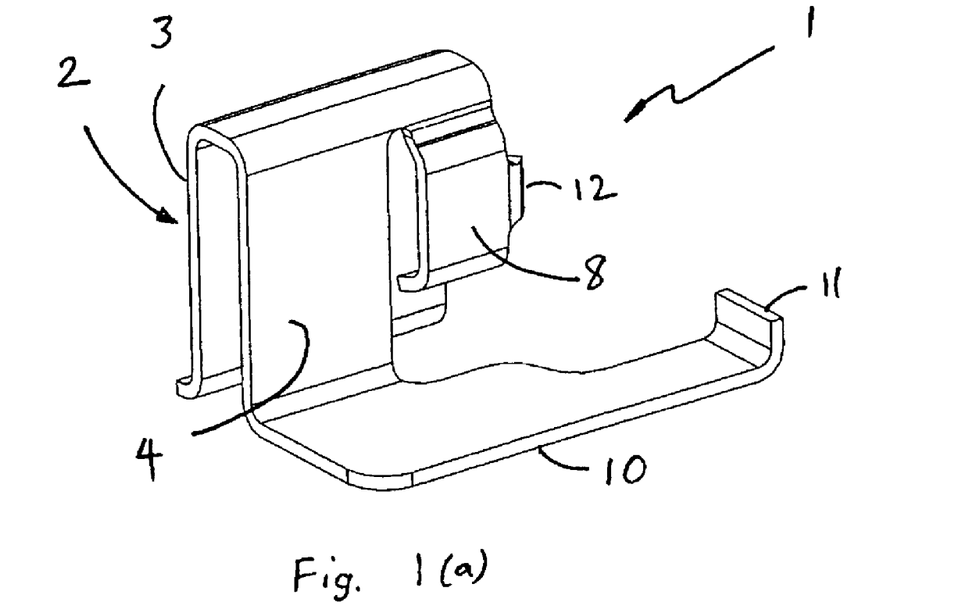
FIG. 1a is a perspective view in a first direction of a plunger lock component of a first embodiment of the invention.
Figure 1B:
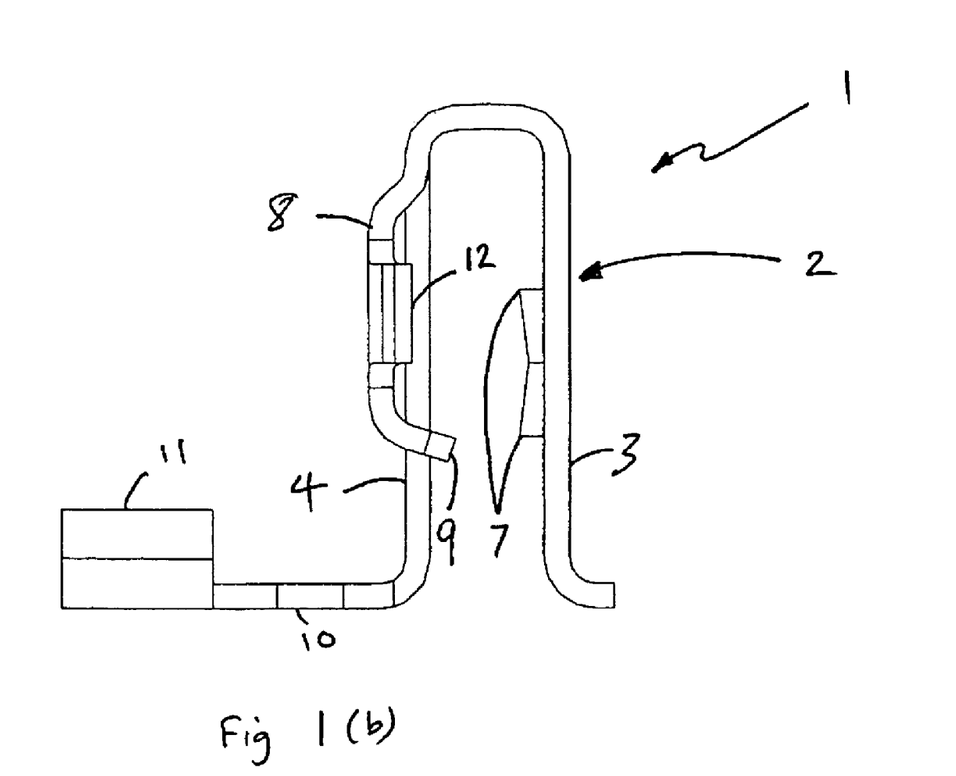
Figure 1C:
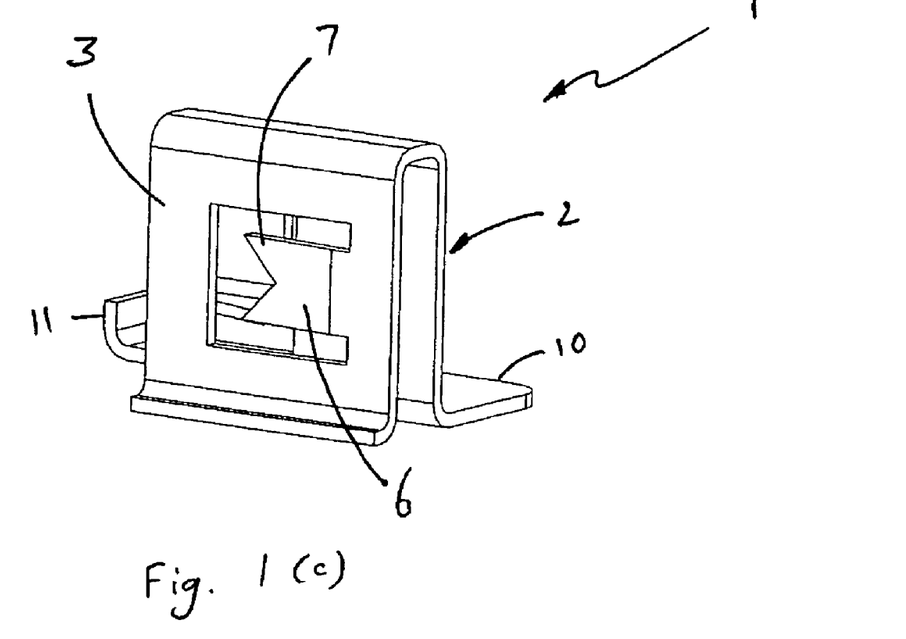
Figure 1D:
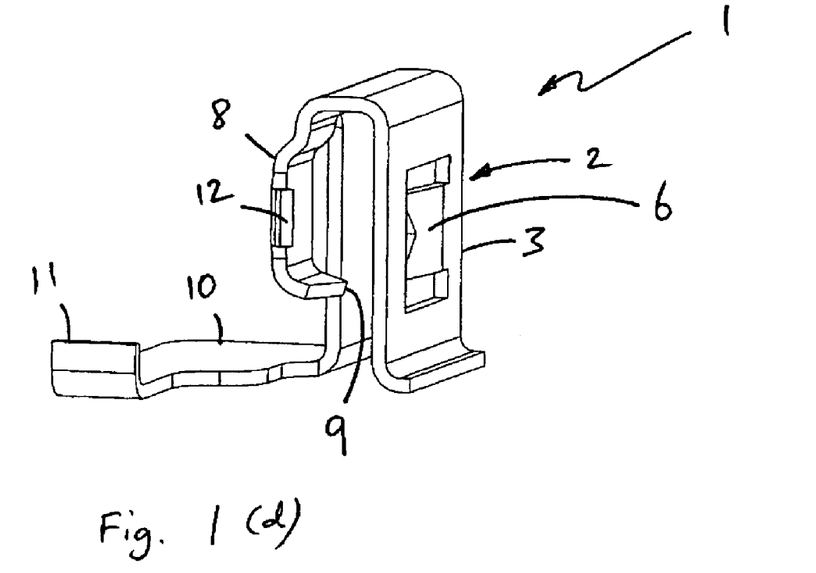
Figure 2A:
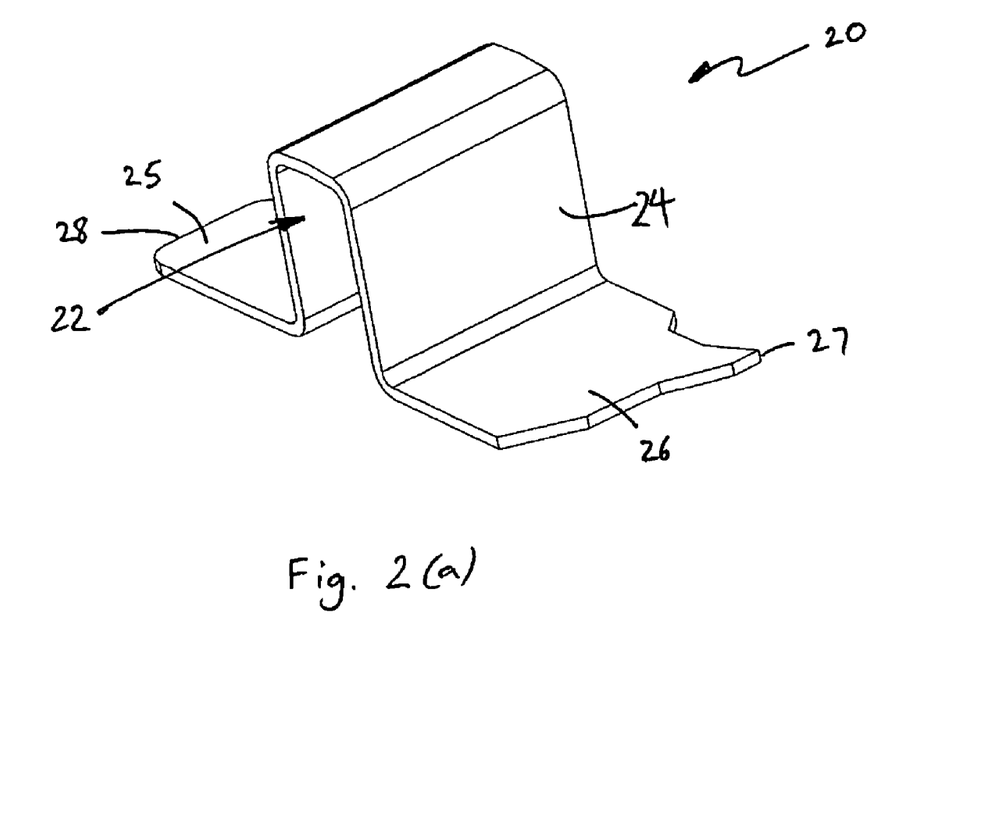
FIG. 2a is a perspective view of a barrel lock component of the first embodiment.
Figure 3:
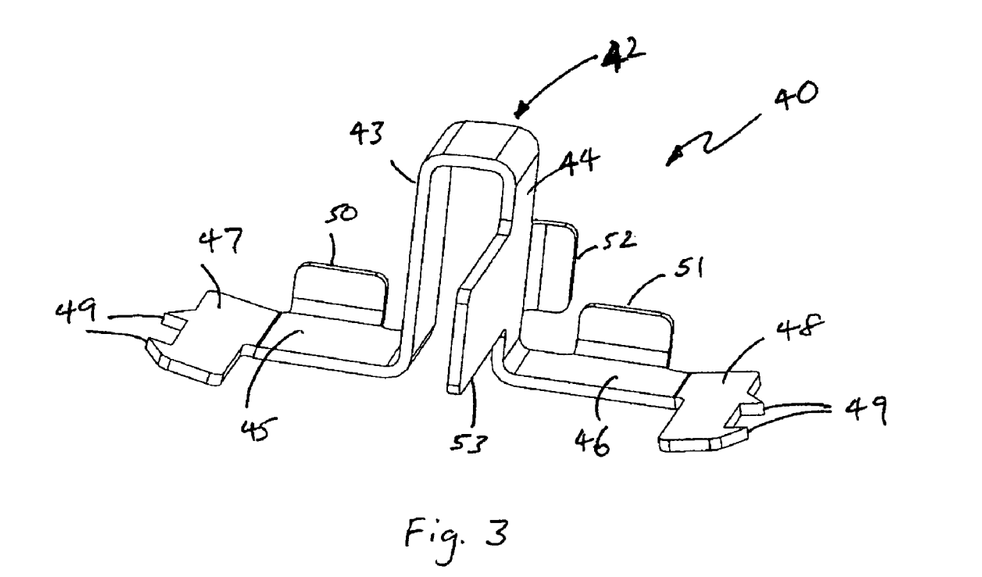
FIG. 3 is a perspective view of a lock release component of the first embodiment.

The first embodiment is based on a standard 5 ml syringe with a cruciform section plunger shaft. Fitted between the plunger shaft and the barrel is a restrictor element. In this embodiment, the restrictor element comprises two pressed stainless steel components 1, 20 termed the plunger lock and the barrel lock and shown, respectively, in FIGS. 1 and 2. An additional component 40, known as the lock release element, is shown in FIG. 3.

Referring firstly to FIG. 1, the plunger lock 1 comprises a unitary body of pressed stainless steel formed into a main arch 2 with first and second side walls 3, 4. The first side wall 3 is wall whose external face is visible in FIGS. 1(*c*) and (*d*) whilst the second side wall 4 is the wall whose external face is visible in FIG. 1(*a*).

The terms "top" and "bottom" as used with reference to this embodiment refer to the top and bottom of the component as it is shown in FIG. 1. The terms "proximal" and "distal" will be used to refer to the right hand end and left hand end, respectively, of the component as it is shown in FIG. 1(*a*), which equates to the left hand end and right hand end as shown in FIG. 1(*c*).

As best seen in FIG. 1(*c*), the first side wall 3 of the main arch 2 is formed with an inwardly and proximally directed tang 6 whose free end is formed with twin points 7. This feature will be termed the distal barb, because it acts to prevent distal movement of the plunger with respect to the restrictor element (the restrictor element in this embodiment being constituted by the plunger lock of FIG. 1 and the barrel lock of FIG. 2).

The second side wall 4 of the main arch 2 (as best seen in FIG. 1(*a*)) is formed with a flap 8 which extends downwardly and outwardly of the second side wall 4 and which then curves back inwardly towards the side wall 4. The free end of the flap 8 is formed as a barb 9 which is positioned so as to engage with the plunger surface when the component is installed on the plunger, and is oriented so as to oppose proximal movement of the plunger. The barb 9 is termed the proximal barb, because it acts to prevent proximal movement of the plunger with respect to the restrictor element.

On the proximal edge of the flap 8 is an inwardly directed flange 1. At the bottom of the second side wall 4 is a laterally and proximally extending tang 10, whose proximal end is formed as an upwardly turned flange 11. The function of these features will be explained later.

Figure 2B:
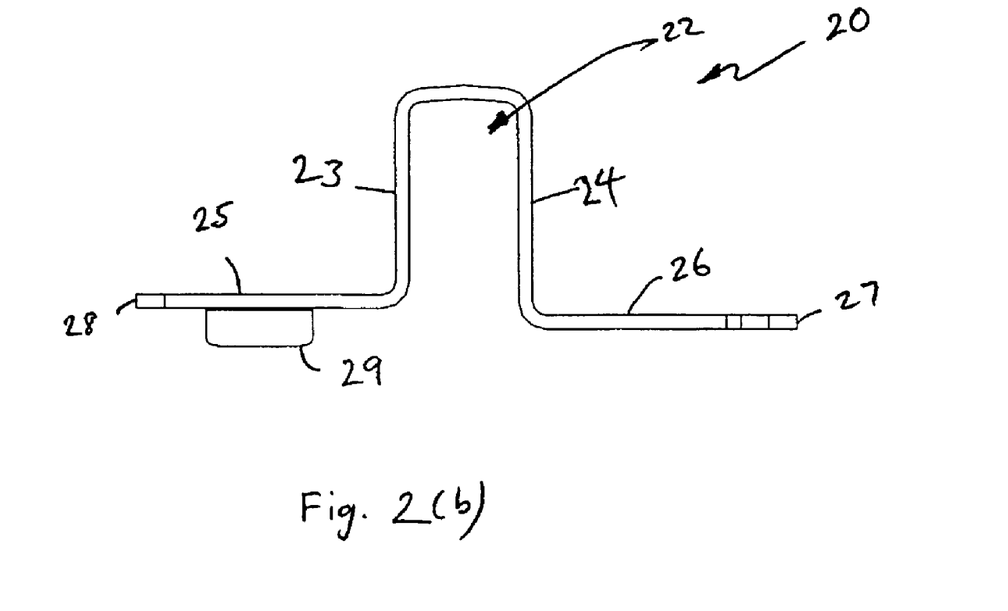
Figure 2C:
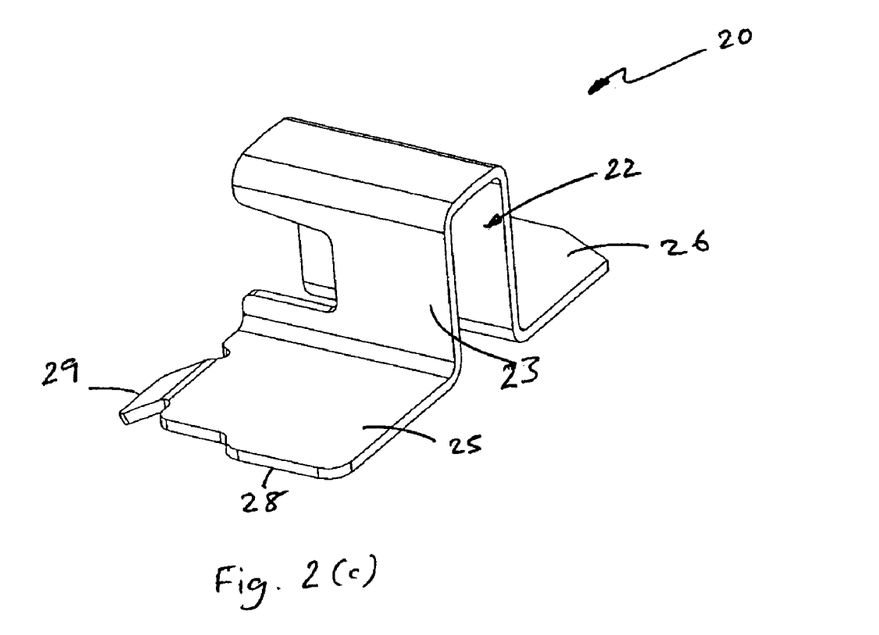

Turning now to FIG. 2, the barrel lock 20 is shown in three views corresponding to those of FIG. 1. Since the views correspond, the terms top, bottom, distal and proximal will be used in the same way, i.e in FIG. 2(*a*) the proximal end is on the right of the figure and the distal end is on the left. It should be noted, however, that the plunger component and barrel component are not both aligned in the same way when they are assembled together as a restrictor bobbin in a syringe (See e.g. FIG. 4).

The barrel lock 20, like the plunger lock, is formed with a main arch 22 having a first side wall 23 and a second side wall 24. Extending laterally from the bottom of each side wall 23, 24 are first and second plates 25, 26 respectively. The proximal outer tip of the second plate 26 is formed as a proximally oriented barb 27 which, when the component is installed in a syringe, bears against the inner wall of the syringe barrel to resist proximal movement of the barrel lock component 20 with respect to the syringe barrel. The outer edge of the first plate 25 has a protrusion 28 with rounded corners which is adapted, in use, to bear against the opposing side of the syringe barrel interior wall, to provide a reaction force for the barb 27.

The proximal end of the first plate 25 is turned downwards at approximately 45 degrees to the plane of the plate 25. The feature is called the lock cinch 29, and its function will be explained later.

Turning now to FIG. 3, a lock release component 40 is shown. This component does not form part of the movable restrictor bobbin which is composed of the plunger lock 1 and the barrel lock 20. The function of the lock release is to "latch" the proximal barb 9 of the plunger lock 1 out of contact with the plunger until an appropriate point in the sequence of operations for using the syringe, i.e. until it is desired to prevent further substantial proximal movement of the plunger.

The lock release component 40 comprises a main arch 42 with first and second side walls 43, 44 respectively. At the bottom of each side wall 43, 44, extend first and second plates 45, 46 respectively. At the outer end of each plate 45, 46 is a respective end region 47, 48 respectively, which is angled slightly upwards out of the place of the plates 45, 46. At the outer end of each end region are twin barbs 49 facing in opposite directions which, when the component is installed in a syringe, engage with the internal wall of the syringe barrel to secure the component against any movement with respect to the barrel. On the proximal side of each of the plates 45, 46 are upwardly turned flanges 50, 51 respectively. There is also an outwardly turned flange 52 on the proximal end of the second side wall 44. These flanges are to assist assembly of the component into a syringe barrel.

Projecting distally from the distal end of the second side wall 44 is a latch tang 53 whose function is to hold the proximal barb 9 of the plunger lock out of engagement with the plunger, as will be explained in more detail below.

The assembled state of the various components of the first embodiment, and its operation, will now be described with reference to FIG. 4 which shows the components assembled on a syringe plunger. The syringe barrel has been omitted for clarity, but its form and location and its interation with the illustrated components will be readily understood by anyone of ordinary skill in this art.

Referring firstly to FIG. 4(*a*) a syringe plunger assembly 60 comprises a plunger shaft 61 of generally cruciform section, that is to say in transverse section will have the shape of a cross with four limbs at 90 degres to each other. The plunger shaft is fitted with an elastomeric plunger or plunger head 62 at its distal end. At its proximal end, the plunger shaft terminates in a disc shaped plate 63 for a use to manipulate the plunger assembly 60. All these components are conventional.

The components of FIGS. 1, 2 and 3 may be seen in their assembled state in FIG. 4. The details are best seen in FIG. 4(*b*) which shows the components somewhat separated. The plunger lock 1 is located with its main arch 2 extending around a first limb 61*a* of the plunger shaft 61, and with its tang 10 extending between the surface of a second limb 61*b* of the plunger shaft 61 and the first side wall 23 of the barrel lock component 20. The plunger lock does not engage with the internal barrel wall.

Figure 4A:
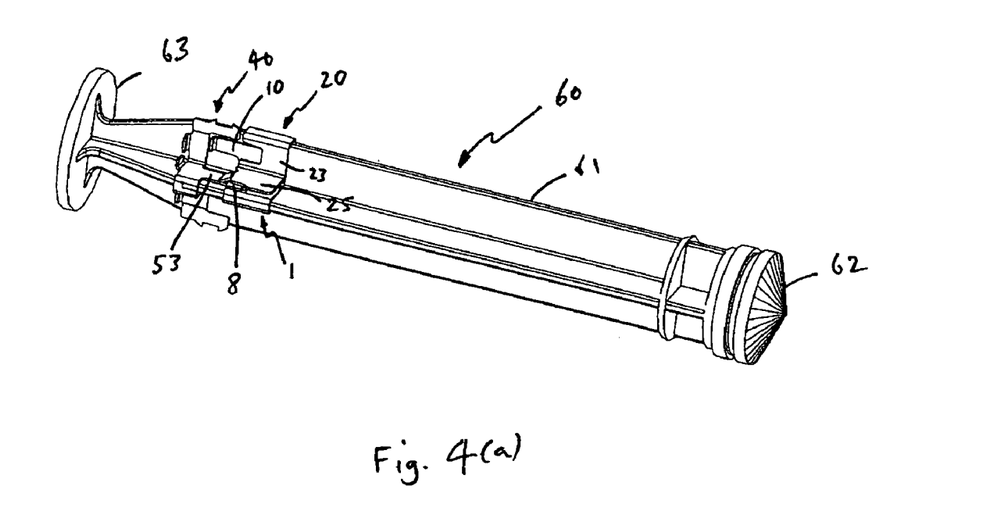
FIG. 4a is a perspective view of a syringe plunger with the components of FIGS. 1, 2 and 3 assembled around it, in its shipped sate (not showing the syringe barrel)
Figure 4B:
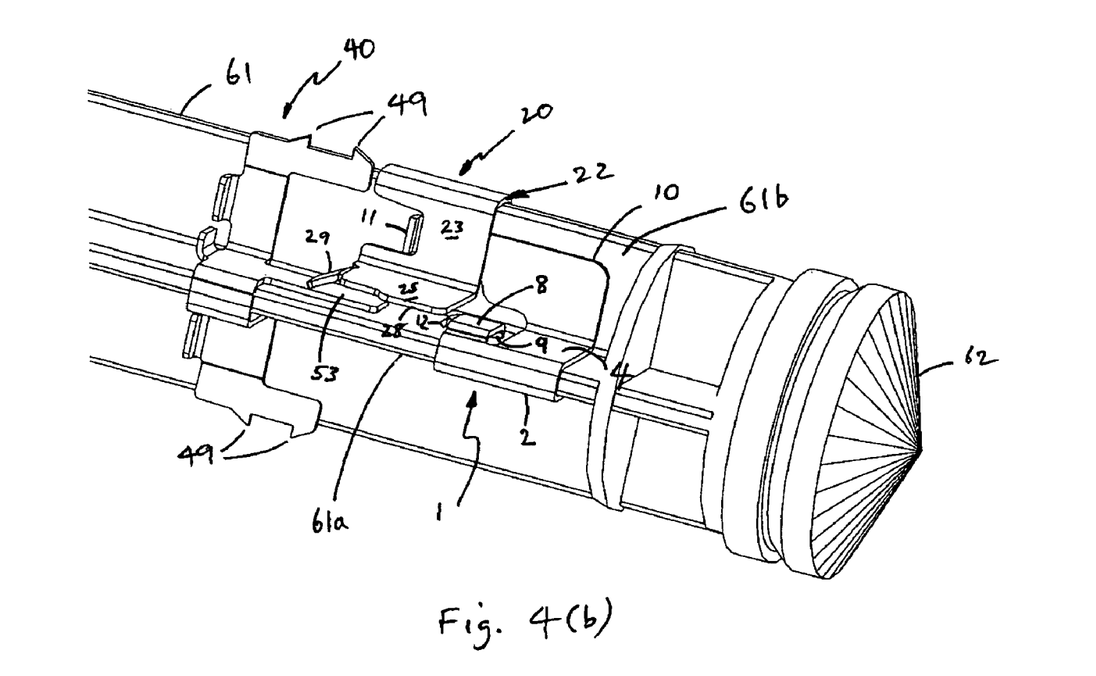
FIG. 4b is a view similar to FIG. 4a showing only part of the plunger and showing the components with the lock release disengaged.

The barrel lock 20 has its main arch 22 extending over the second limb 61*b* of the plunger, which is at 90 degrees to the limb 61*a* over which the plunger lock 1 is mounted. Although the barrel of the syringe is not shown, it will be appreciated that the outer edge 28 of the barrel lock and the barrel lock barb 27, which is hidden behind the plunger in FIG. 4, will bear against opposing regions of the inner surface of the barrel wall. The barrel lock has no other barb and is thus freely movable with respect to the plunger, unless its movement is limted by engagement with another component of the device e.g. the plunger lock 1.

The lock release 40 is disposed with its main arch 42 extending around the first limb 61 a of the plunger shaft 61. Opposed barbs 49 of the lock release may be seen clearly in FIG. 4b; these are engaged with the barrel in a manner which will be understood readily by someone of ordinary skill in this art, such that the lock realease 40 is immovably retained with respect to the barrel. There are no other barb elements on the lock release, and thus the plunger shaft and lock release are freely movable with respect to each other.

The device is shown in its shipped state in FIG. 4(a). In this figure, the plunger should be assumed to be fully or substantially fully depressed into the barrel, i.e. substantially at its most extreme distal position. The three pressed steel components 1, 20 and 40 are all located in the region of the proximal end of the barrel and plunger. The latch tang 53 of the lock release 40 extends between the first limb 61a of the plunger shaft and the flap 8, flange 12 and proximal barb 9 of the plunger lock 1. The first side wall 23 of the barrel lock 20 extends over the tang 10 of the plunger lock and the first plate 25 of the barrel lock extends over the first side wall 4 and flap 8 of the plunger lock 1.

The proximal barb 9 of the plunger lock is biased towards the first limb 61a of the plunger shaft by virtue of the geometry of the main arch 2 and the resilience of the stainless steel of which it is made. At the same time the distal barb 6 of the plunger lock (hidden in FIG. 4) is biased towards the opposite side of the first limb 61a of the plunger shaft. Whilst the distal barb 6 engages with the plunger shaft to resist distal movement of plunger with respect to the plunger lock, the latch tang 53 of the lock release 40 comes between the proximal barb 9 and the plunger and prevents the proximal barb 9 from engaging with the plunger shaft. The proximal barb 9 may slide relatively freely over the latch tang 53 since the latch tang 53 is made of stainless steel rather than the polypropylene of the plunger shaft.

The first operation when the syringe is used is to draw back the plunger, normally either to draw up a liquid medicament or to draw up a blood sample from a patient. As the plunger is drawn back (i.e. moved in the proximal direction), the shaft moves freely past the lock release 40 and barrel lock 20. The distal barb 6 of the plunger lock is biased against the plunger shaft, but the barb is oriented so as not to create substantial resistance to proximal movement of the plunger. The plunger lock 1 is prevented from moving proximally by engagement of the flap 8 and flange 12 on the plunger lock with the lock cinch 29 of the barrel lock 20. The interaction of the cinch 29 with the flange 12 to prevent proximal movement of the plunger lock 1 with respect to the barrel lock 20 is shown more clearly in FIG. 4(e). Thus the components remain essentially in their shipped state as shown in FIG. 4(a) whislt the plunger is retracted either fully or partially.

The plunger of the syringe is then depressed (i.e. moved distally) to expel the contents which have been drawn up. The state of the components after an initial small movement of the plunger in the distal direction is shown in FIG. 4(b). As the plunger moves distally, the plunger element 1 moves with it since the distal barb 6 acts to prevent relative movement of the plunger element and plunger shaft in this sense. Since the lock release 40 is fixed to the barrel, the proximal barb 9 of the plunger lock 1 slides off the latch tang 53 as the plunger moves distally. FIG. 4(b) shows the proximal barb disengaged from the latch tang 53 and bearing against the first limb 61a of the plunger shaft.

The barrel lock 20 remains in its shipped state until, as the plunger lock 1 moves distally, the flange 11 at the proximal end of the tang 10 of the plunger lock 1 engages with the proximal edge of the first side wall 23 of the barrel lock 20, as shown in FIG. 4(b). At this point the barrel lock 20 is drawn along with the plunger lock 1; the barb 27 of the plunger lock is engaged with the interior wall of the barrel (not shown) but the orientation of the barb 27 is such that distal movement of the barrel lock in the barrel is not resisted.

Figure 4C:
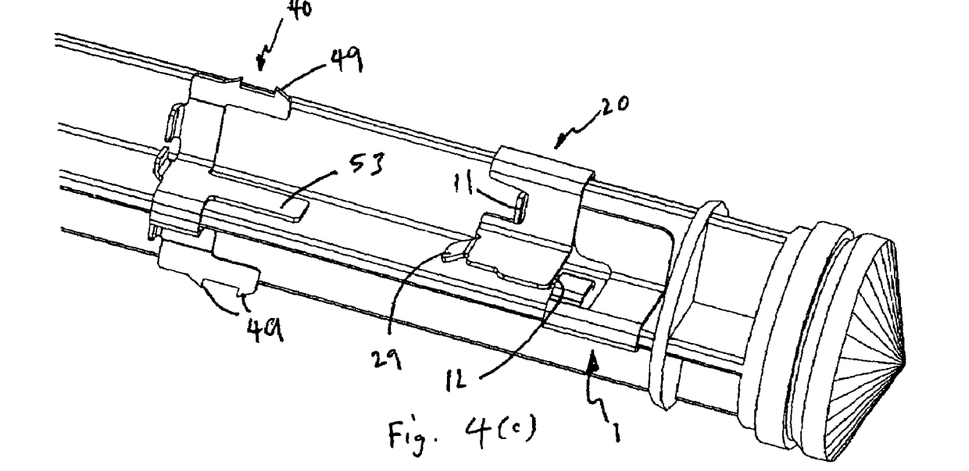
FIG. 4c is a view similar to FIG. 4b showing the components during expulsion of fluid from the syringe.

FIG. 4(c) shows a state when the plunger has been depressed further to expel the contents of the syringe. If the syringe had been only partly filled prior to commencing expulsion of its contents, then FIG. 4(c) might show the fully depressed state of the plunger. The barrel should be imagined as having its internal distal end face adjacent the plunger head in FIG. 4(c), i.e. with substantially no volume remaining within the barrel.

Figure 4D:
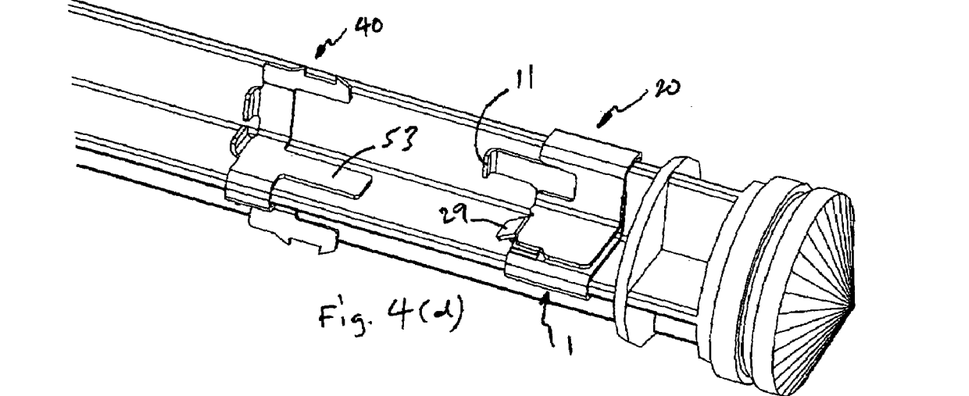
FIG. 4d is a view similar to FIG. 4b showing the components in a challenged state after drawing up and expulsion of less than a full syringe of liquid.
Figure 4E:
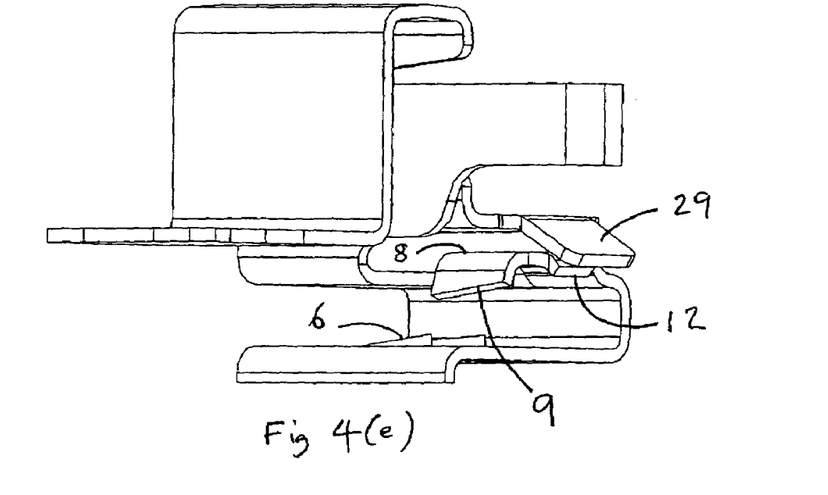
FIG. 4e is a perspective view of the components of FIGS. 1, 2 and 3 in a challenged state, with the syringe plunger and barrel omitted.

FIG. 4(d) shows the state of the components if a user attempts to draw back the plunger from the state shown in FIG. 4(c), i.e. to draw up a further volume of liquid in order to re-use the syringe. As the plunger is drawn back, the plunger lock is forced to move back with it because the proximal barb 9 on the plunger lock acts to prevent proximal movement of the the plunger relative to the plunger lock. The plunger and plunger lock move proximally until the flange 12 on the plunger lock encounters the lock cinch 29 on the barrel lock. At this point, no further proximal movement is possible because the barrel lock barb 27 prevents proximal movement of the barrel lock with respect to the plunger.

Additional security is provided in this design by the design of the cinch 29 and flange 12. These components are angled such that increased force on the plunger to withdraw it will cause increased force on the barb 9 in the direction of the surface of the first plunger limb 61a, thereby increasing the resistance of the plunger lock against proximal movement.

It will be appreciated that the barrel lock 20 and plunger lock 1 allow unlimited repeated movement of the plunger over a distance which is limited at one end by the engagement of the cinch 29 and flange 12 (FIGS. 4(d) and 4(c)), and at the other end by engagement of the flange 11 with the proximal edge of the first side wall 23 of the barrel lock (see FIGS. 4(b) and 4(c)). As discussed in relation to the other embodiments, this movement allows for withdrawal of a flash of blood prior to administering an injection to check the position of the needle in a patient.

A second embodiment will now be described with reference to FIGS. 5 to 8. Similar to the first embodiment, this embodiment incorporates the additional safety feature of preventing re-use of the syringe even if the first use does not involve completely filling the syringe. The second embodiment also incorporates the "lost motion" feature, as with all the other embodiments, which allows unrestricted free movement of the plunger over a limited distance. The second embodiment differs from the first in that these objectives are achieved with only two components in addition to the standard syringe components.

Figures 5A, 5B, 6A, 6B:
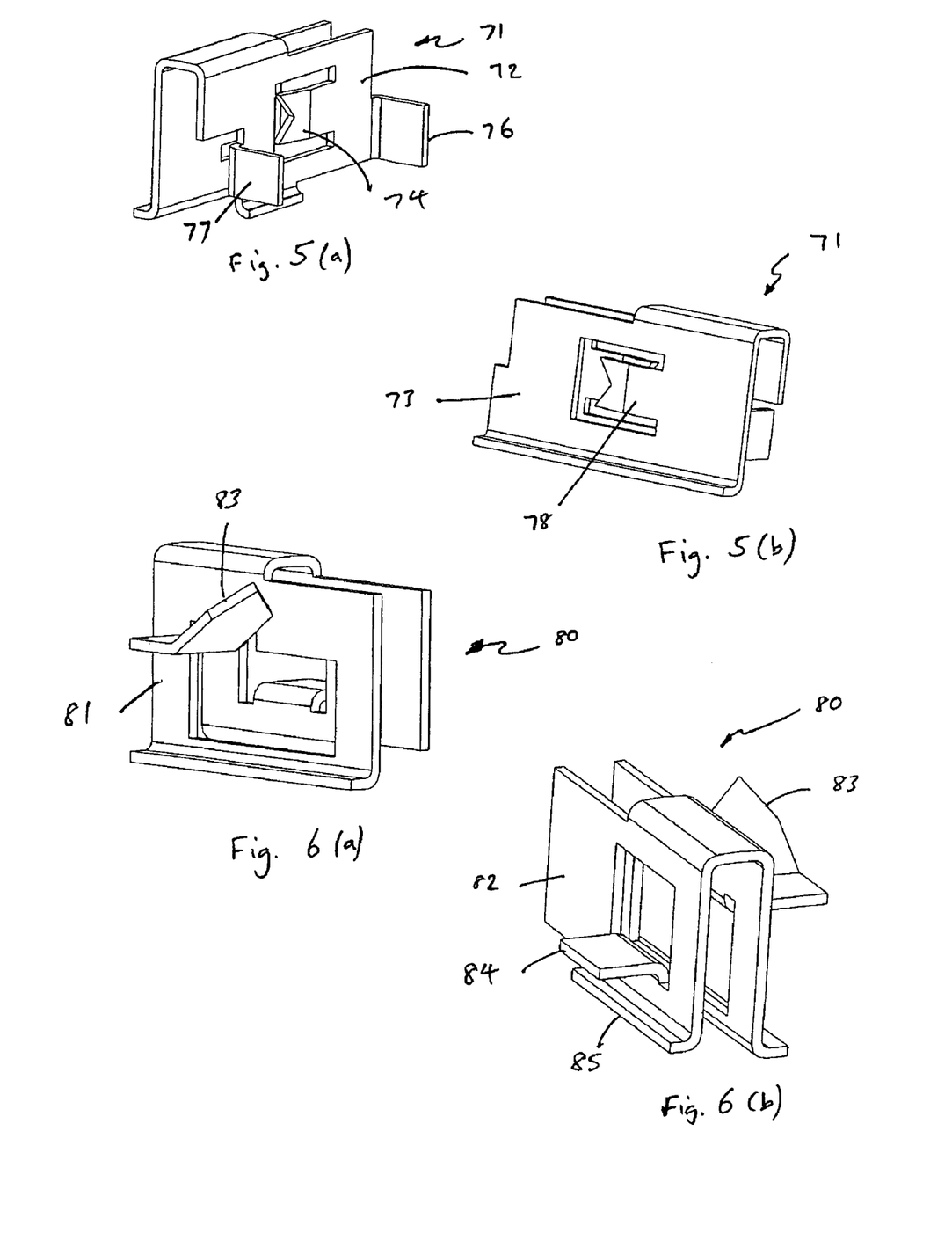

FIG. 5 shows a plunger lock component 71 of pressed stainless steel. The proximal end of the component is to the right in FIG. 5(a). The terms "top" and "bottom" regarding this component will be used for this component as it is represented in FIG. 5(a). The component comprises a general U shape with first and second side walls 72, 73. In the first side wall 72 is an aperture from which projects a barb 74 which is oriented inwardly so as to resist proximal movement of the plunger with respect to the plunger lock 71; this will be referred to as the proximal barb 74. At each end of the first wall 72 are proximal and distal flanges 76, 77 respectively. In the second wall 73 (see FIG. 5(b)) is a further aperture from which projects a further barb 78 which is oriented inwardly so as to resist distal movement of the plunger with respect to the plunger lock 71; this will be referred to as the distal barb 78.

FIG. 6 shows a plunger lock 80 also comprising a generally U shaped member of pressed stainless steel having first and second side walls 81, 82 respectively. The proximal end of the plunger lock 80 is the right hand end as it is represented in FIG. 6(a). The terms "top" and "bottom" will be used as they relate to the component as it is depicted in FIG. 6(a), though it should be bourne in mind that, as with the first embodiment, the plunger lock and barrel lock are not oriented in the same sense when installed in a syringe (see FIGS. 7 and 8).

Projecting laterally and proximally from the first side wall 81 of the barrel lock, and inclined upwardly, is a barb 83 oriented to resist movement of the barrel lock in a proximal direction; this is referred to as the proximal barb 83 on the barrel lock. On the second side wall 82 of the barrel lock is a laterally extending limiting flange 84. The base of the second wall 82 is turned outwardly to form a latch flange 85. The function of these flanges will be explained later.

Figure 7:
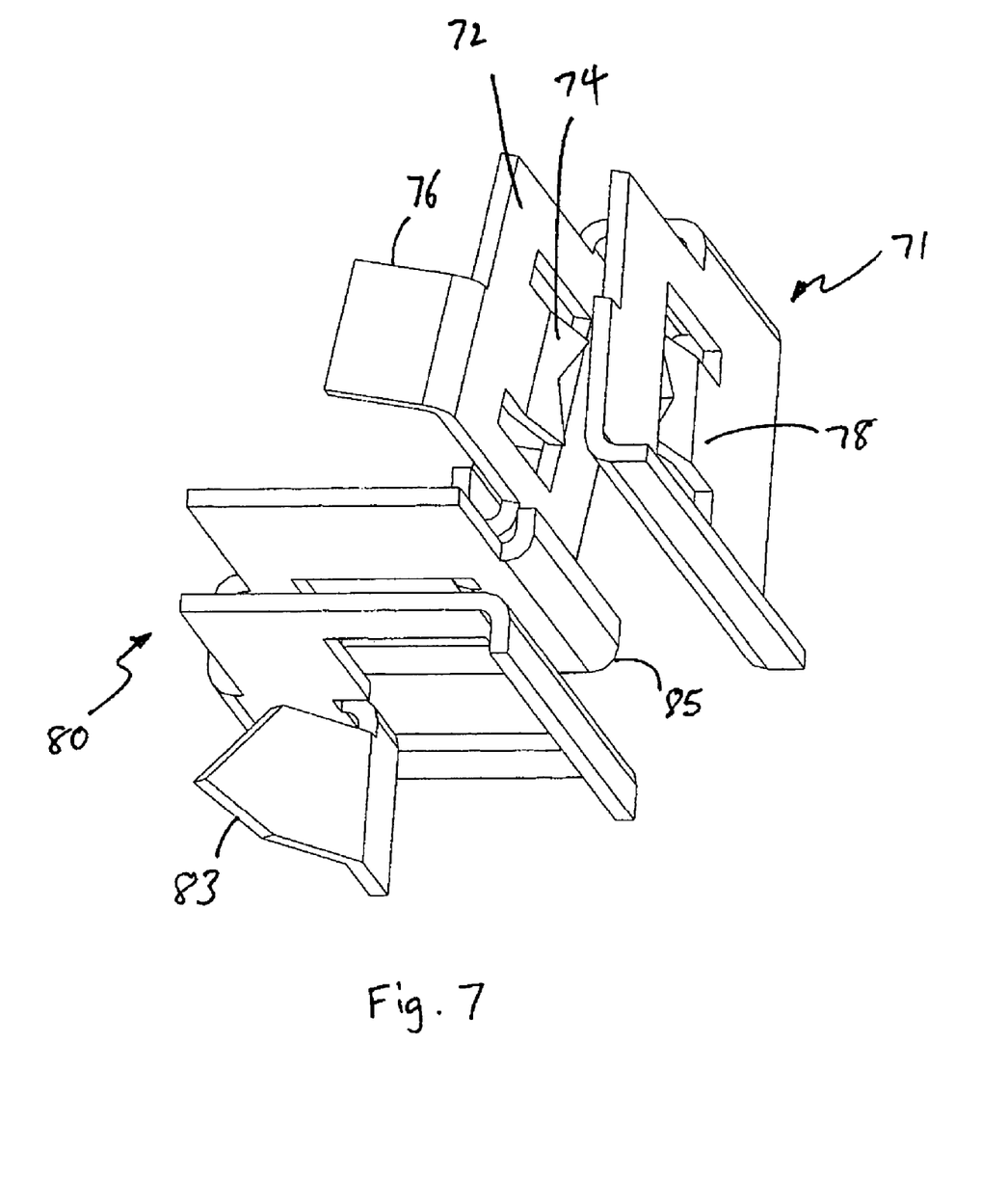
FIG. 7 is a perspective view of the plunger lock and barrel lock components in an assembled state, omitting the syringe barrel and plunger.
Figure 8A:
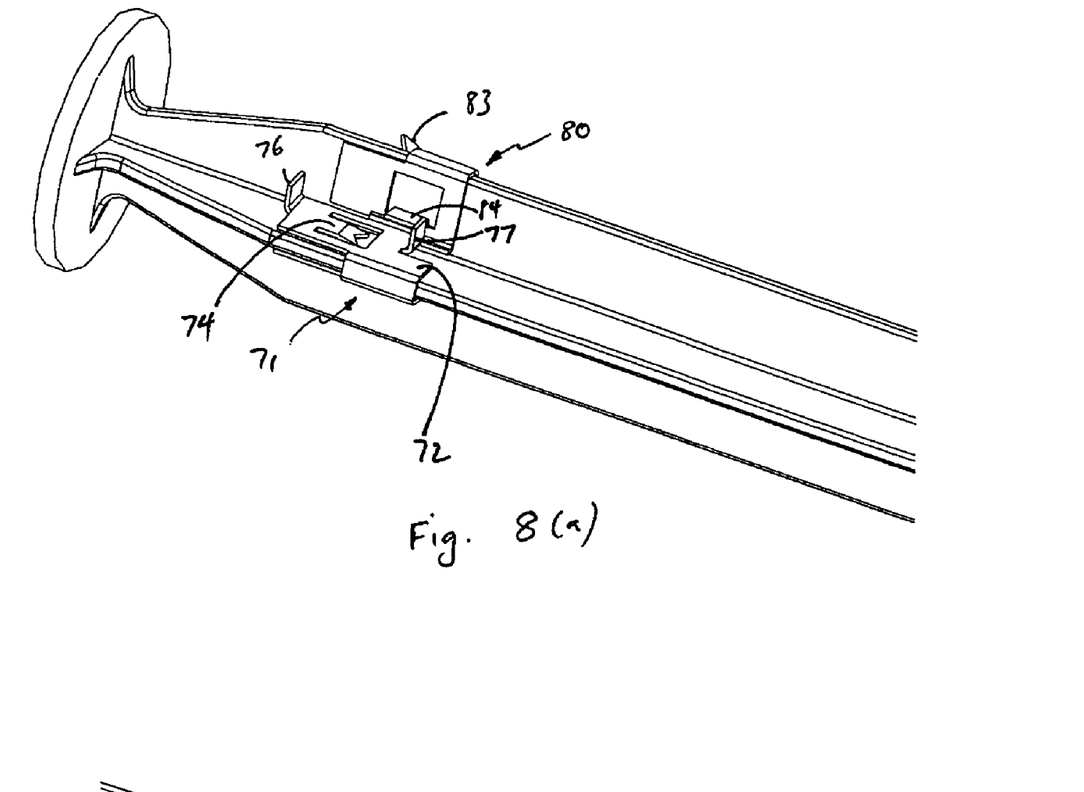
FIG. 8a is a perspective view of part of a syringe plunger with the components of FIGS. 5, 6 and 7 assembled around it, in its shipped sate (not showing the syringe barrel)

FIG. 7 shows the plunger and barrel locks in their shipped state with the plunger and barrel hidden. The components are shown in the same state in FIG. 8(a) with the plunger shown; in FIG. 7 the components have been represented in an orientation which shows the latch flange 85 of the barrel lock engaged with the first side wall 72 of the plunger lock 71 so as to hold the proximal barb 74 out of contact with the plunger.

Figure 8B:
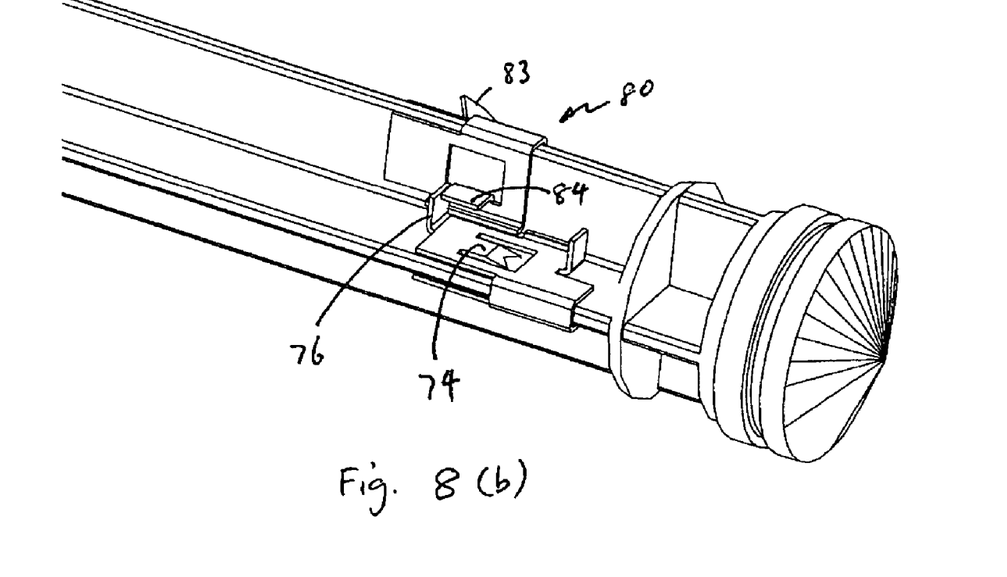
FIG. 8b is a view similar to FIG. 8a showing the components during expulsion of fluid from the syringe.

The function of the various components will be apparent from the drawings. In the shipped state, shown in FIG. 8(a) and FIG. 7, the proximal barb 74 does not prevent proximal movement of the plunger which can therefore be retracted to draw up fluid. Initial distal movement of the plunger, as with the first embodiment, causes the latch 85 to be released; as the plunger moves distally is carries the plunger lock with it and the first side wall of the plunger lock slips off the latch 85, allowing the proximal barb 74 to engage the plunger. Thereafter, further movement of the plunger in the distal direction causes the proximal flange on the plunger element to engage with the limiting flange 84 of the barrel lock thereby dragging the barrel lock with it. This state is shown in FIG. 8(b).

As with the first embodiment, once the latch 85 is disengaged, proximal movement of the plunger becomes impossible, apart from the limited free movement allowed by the relative movement between the plunger and barrel locks (limited by the proximal and distal flanges 76, 77 on the plunger lock engaging with the limiting flange 84 on the barrel lock). This is because the barb 83 on the barrel lock prevents proximal movement of the barrel lock, the plunger lock cannot move proximally with respect to the barrel lock because of interaction between the flanges 84 and 76, and the plunger cannot move proximally past the plunger lock because of the proximal barb 74.

Modified forms of the first and second embodiments are contemplated where the barrel lock component is provided with a distal barb or the like in addition to its proximal barb, and the plunger lock is provided only with its distal barb. In these modified embodiments, a latch member would be provided to prevent engagement of the distal barb of the barrel lock until the plunger has been drawn back and then expulsion of fluid has commenced. The latch could be provided e.g. as a projection on the plunger lock or alternatively on a separate member as in the first embodiment. In the latter case, the separate member would be mounted on the plunger, most appropriately on or adjacent the proximal side of the plunger head.

A potential issue with the first and second embodiments is that there may be a small jerk when the latch is disengaged as the plunger is initially depressed. As previously stated, this could potentially cause discomfort to a patient if the needle has been inserted into the patient at this point. However, it is a simple matter to make the initial movment of the plunger prior to insertion of the needle into the patient, and in fact this is normal practice in order to expel any air in the syringe prior to administering an injection.

The invention claimed is:

1. A syringe comprising:
   (a) a plunger including a plunger head and a shaft;
   (b) a barrel;
   (c) a restrictor mechanism located between the shaft and the barrel and including (i) a first part having an outer member engaged with the barrel and oriented so as to limit movement of the first part with respect to the barrel in a first direction, and (ii) a second part;
   (d) the restrictor mechanism and/or shaft carrying a formation for limiting movement of the restrictor mechanism with respect to the plunger in said first direction;
   (e) the restrictor mechanism being provided with a further member oriented or arranged so as to restrict movement of the restrictor mechanism with respect to one of the barrel and plunger shaft in a second direction opposed to said first direction; and
   (f) a latch member for preventing the further member from restricting movement of the restrictor mechanism with respect to one of the barrel and plunger shaft in said second direction until a predetermined point in an operation cycle of the syringe;
   wherein the first part and second part are moveable relative to each other over a limited range of movement to permit unlimited repeated movement of said plunger relative to the barrel in said first and second directions over said limited range.

2. A syringe as claimed in claim 1 wherein the said predetermined point in the operation cycle is an initial movement of the plunger in a distal direction.

3. A syringe as claimed in claim 1 wherein the barrel has a cylindrical interior surface substantially free of discontinuities between proximal and distal ends of a full range of usable movement of a plunger head in the barrel.

4. A syringe as claimed in claim 1 wherein the said formation carried by the restrictor mechanism and/or shaft for limiting movement in the first direction comprises a member which is engaged with the plunger shaft surface.

5. A syringe as claimed in claim 1 wherein the plunger and restrictor mechanism are freely slidable with respect to each other over a limited range of movement, or the plunger or restrictor mechanism have relatively movable parts, whereby unlimited repeated proximal and distal cycles, of plunger head movement with respect to the barrel are permitted over a predetermined limited range which is less than said full usable range of movement of the plunger head.

6. A syringe as claimed in claim 1 wherein the said latch member comprises a separate member secured to the barrel.

7. A syringe as claimed in claim 6 wherein the said latch member comprises a projection which, in an engaged state, extends distally between the plunger shaft and the said further member on the restrictor mechanism.

8. A syringe acclaimed in claim 5 wherein the restrictor mechanism comprises two relatively movable parts, and wherein the said latch member comprises a projection extending from one of the said parts of the restrictor mechanism.

9. A syringe as claimed in claim 7 wherein the said projection extends between the plunger or barrel surface and the said further member on the other of the said two parts of the restrictor mechanism.

10. A syringe as claimed in claim 1 wherein the said latch member comprises a separate member secured on or adjacent the proximal side of the plunger head, which in an engaged state extends between the barrel interior wall and a portion of the restrictor mechanism.

* * * * *

UNITED STATES PATENT AND TRADEMARK OFFICE
CERTIFICATE OF CORRECTION

PATENT NO.       : 7,588,556 B2
APPLICATION NO. : 11/155888
DATED            : September 15, 2009
INVENTOR(S)      : Byrne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 782 days.

Signed and Sealed this

Twenty-first Day of September, 2010

David J. Kappos
*Director of the United States Patent and Trademark Office*